United States Patent [19]

Mimura et al.

[11] Patent Number: 5,298,744
[45] Date of Patent: Mar. 29, 1994

[54] MASS SPECTROMETER

[75] Inventors: Tadao Mimura, Katsuta; Yoshiaki Kato, Mito; Kazumi Matsumura, Toukai, all of Japan

[73] Assignee: Hitachi, Ltd., Tokyo, Japan

[21] Appl. No.: 12,469

[22] Filed: Feb. 2, 1993

[30] Foreign Application Priority Data

Feb. 4, 1992 [JP] Japan .................................. 4-018121

[51] Int. Cl.⁵ .............................................. H01J 49/10
[52] U.S. Cl. ..................................... 250/288; 250/281
[58] Field of Search ................... 250/288, 288 A, 281, 250/282

[56] References Cited

U.S. PATENT DOCUMENTS

| | | | |
|---|---|---|---|
| 4,016,421 | 4/1977 | Hull et al. | 250/288 A |
| 4,531,056 | 7/1985 | Labowsky et al. | 250/288 |
| 4,935,624 | 6/1990 | Henion et al. | 250/288 |
| 4,977,320 | 12/1990 | Chaudhury et al. | 250/288 |
| 5,130,538 | 7/1992 | Fenn et al. | 250/288 |
| 5,235,186 | 8/1993 | Robins | 250/288 |

OTHER PUBLICATIONS

Sakairi et al "Characteristic of a Liquid Chromatograph/Atmospheric Pressure Ionization Mass Spectrometer" Anal. Chem. 1988, 60, pp. 774-780.

Huang et al. "Atmosphere Pressure Ionization Mass Spectrometry" Anal. Chem 1990, vol. 62, pp. 713A-725A.

Primary Examiner—Paul M. Dzierzynski
Assistant Examiner—Kiet T. Nguyen
Attorney, Agent, or Firm—Antonelli, Terry, Stout & Kraus

[57] ABSTRACT

Ions generated by an ES ion supply are introduced into a mass spectrometer portion through a small hole in a second electrode after passing through a small hole in a heated first electrode, and are analyzed by a mass spectrometer. Corresponding to heating of the first electrode, a length of the small hole in the first electrode is determined to a predetermined adequate value.

15 Claims, 4 Drawing Sheets

MASS SPECTROMETER

BACKGROUND OF THE INVENTION

(1) Field of the Invention

The present invention relates to a mass spectrometer, especially to a mass spectrometer suitable for mass spectrometry of ions which are formed by an atmospheric pressure ionization.

(2) Description of the Prior Art

A liquid chromatography directly coupled with mass spectrometry utilizing an electro-spray ionization (ESI), which is a type of atmospheric ionizations (LC/ESI-MS), has such a feature that fragment ions of a sample are less likely to be produced in comparison with a gas chromatography directly coupled with mass spectrometry utilizing conventional electron impact ionization (EI), because the sample is ionized moderately. In particular, observation of pseudo-molecular ions and multi-charged ions in measurement of high molecules, such as peptide, can be facilitated.

In accordance with the LC/ESI-MS processes utilizing an ESI, a sample and a mobile phase, which are eluates from a liquid chromatograph, are supplied into an ESI probe through a capillary tube, and are neutralized at a top end of the probe with assistance from a nebulizer gas and a high electrostatic field. The nebulized sample molecules are ionized and accelerated under a high electric field so as to pass through a small hole in a first electrode, and are supplied into a medium pressure region which is formed between the first electrode and a second electrode.

At the beginning of the nebulization, the sample molecule is in the form of a small droplet in which a sample molecule is wrapped with the mobile phase (an eluent film for the sample), and is in a charged condition with a high voltage (about 5–8 kV) which is charged with the sample pipe.

A droplet of the nebulized sample is gradually reduced in size owing to evaporation of components in the mobile phase and ejects a sample molecular ion into a gas phase before reaching the first electrode.

That means, when the sample droplet becomes small, a Coulomb repulsive force between the sample ion and an electrostatic force in the mobile phase becomes larger than the surface tension of the mobile phase layer which exists on the surface of the sample particle, and the sample ions in the sample droplet are released from the mobile phase layer and change to ions of only sample molecules. The above phenomenon is called "ion evaporation".

The sample molecular ions are transferred to a stage for mass spectrometry through a small hole in the first electrode and a small hole in the second electrode, and are analyzed by the mass spectrometer. At the mass spectrometry stage, the analytical sensitivity is improved with the injected sample molecular ions having less dispersed distribution of masses.

Furthermore, the larger the ionization tendency of the sample, the higher will be the efficiency of the ion evaporation. Accordingly, the above mass spectrometer is suitable for analyzing a high polymer sample having strong polarities of NH, OH, and CO etc, such as a peptide, for example, with a high sensitivity. Consequently, the spectrometer has attracted a great deal of attention, especially in the field of medical analysis. On the contrary, an analysis of the above high polymer sample by a gas chromatograph direct connection type mass spectrometer (GC/MS) has been impossible because the sample is thermally destroyed easily.

However, actual sample molecules which are ionized by the ion evaporation inevitably still include a large number of mobile phase molecules, especially water molecules, and so sample molecular ions adsorbing water molecules pass through the small hole in the second electrode, although the water molecules are partially dissociated by collisions with neutral molecules when passing through the medium pressure region.

The sample molecular ions adsorbing water molecules collide with neutral particles in a free space at an entrance of an electric field for velocity dispersion in the mass spectrometry stage and a following electric field, and the water molecules are dissociated.

The number of the dissociated water molecules from a sample molecule have been calculated from the width of the kinetic energy of the sample molecular ions which pass through the electric field and are formed to be 30 to 60 molecules.

Similarly, the sample molecular ions dissociate water molecules by collisions with neutral particles in the space from an outlet of the electric field to an outlet of a magnetic field for mass dispersion.

Although a large number of water molecules are dissociated in a manner described above before reaching the entrance of the magnetic field, if the residual amount of water molecules is large, a dispersion of distribution in mass of the sample molecular ions becomes large, and consequently, the analytical sensitivity decreases because not all of the sample molecular ions are able to reach the detector.

A method which proposes to solve the above described problem is disclosed in U.S. Pat. No. 4,977,320 (Chowdhury, Katta, and Chait). In accordance with Chowdhury et al, a capillary tube which is wound with a heater is installed in front of the first electrode, and a nebulized sample which is injected from an ESI probe is introduced into the capillary tube.

The capillary tube is located between an atmospheric pressure region and a reduced pressure region, and accordingly, restricts gas flow into the reduced pressure region by its flow resistance, concurrently extends the residence time for the nebulized sample which is injected from the ESI probe to reach the small hole in the first electrode, and increases the efficiency of ion evaporation. As a result, an effect for homogenizing the mass of the sample molecular ions is assumed to be increased.

However, the temperature of the nebulized sample decreases while passing through the capillary tube as a result of adiabatic expansion, and consequently, the efficiency of the ion evaporation decreases. But, this undesirable affect on the efficiency can be overcome by elevating the temperature of the nebulized sample with the heater which is wound around the capillary tube.

For instance, in a case of the ESI mass spectrometer disclosed in U.S. Pat. No. 4,977,320, a capillary tube having 0.5 mm in inside diameter and 10–20 cm in length is used, but fabrication of such a capillary tube is very difficult in practice.

Furthermore, washing of the capillary tube necessary for maintenance is difficult, fixing of the capillary tube and an axial adjustment of the tubes during that replacement are troublesome, and the winding of the heater on the capillary tube is difficult. Additionally, a biomolecule sample, such as a peptide, decomposes easily by over-heating, and consequently, it is necessary to keep the heating temperature of the capillary tube below approximately 80° C. when the sample passes through a long capillary tube for a relatively long time.

SUMMARY OF THE INVENTION

One of the objects of the present invention is to provide a mass spectrometer which is preferable for use with an ESI. Another one of the objects of the present invention is to provide a mass spectrometer which is effective in solving the above described problems.

A further one of the objects of the present invention is to provide a mass spectrometer which is capable of improving sensitivity when observing a multicharged ion.

Furthermore, another one of the objects of the present invention is to provide a mass spectrometer which makes it possible to eliminate mobile phase in an eluent from a liquid chromatograph effectively when used with the liquid chromatograph.

In accordance with the present invention, there is provided a mass spectrometer comprising means for ionizing a sample so as to generate sample ions, a first electrode having a first hole for passing the generated sample ions, a second electrode having a second hole for passing the ions which have passed through the first hole, means for performing mass spectrometry on the ions which have passed through the second hole, and means for heating the inside of the first hole, the first hole being substantially at most 50 mm in length.

Other features and objects of the present invention will be apparent from the following description taken in connection with the accompanying drawings.

DETAILED DESCRIPTION OF THE PREFERRED EMBODIMENTS

Figure 1:
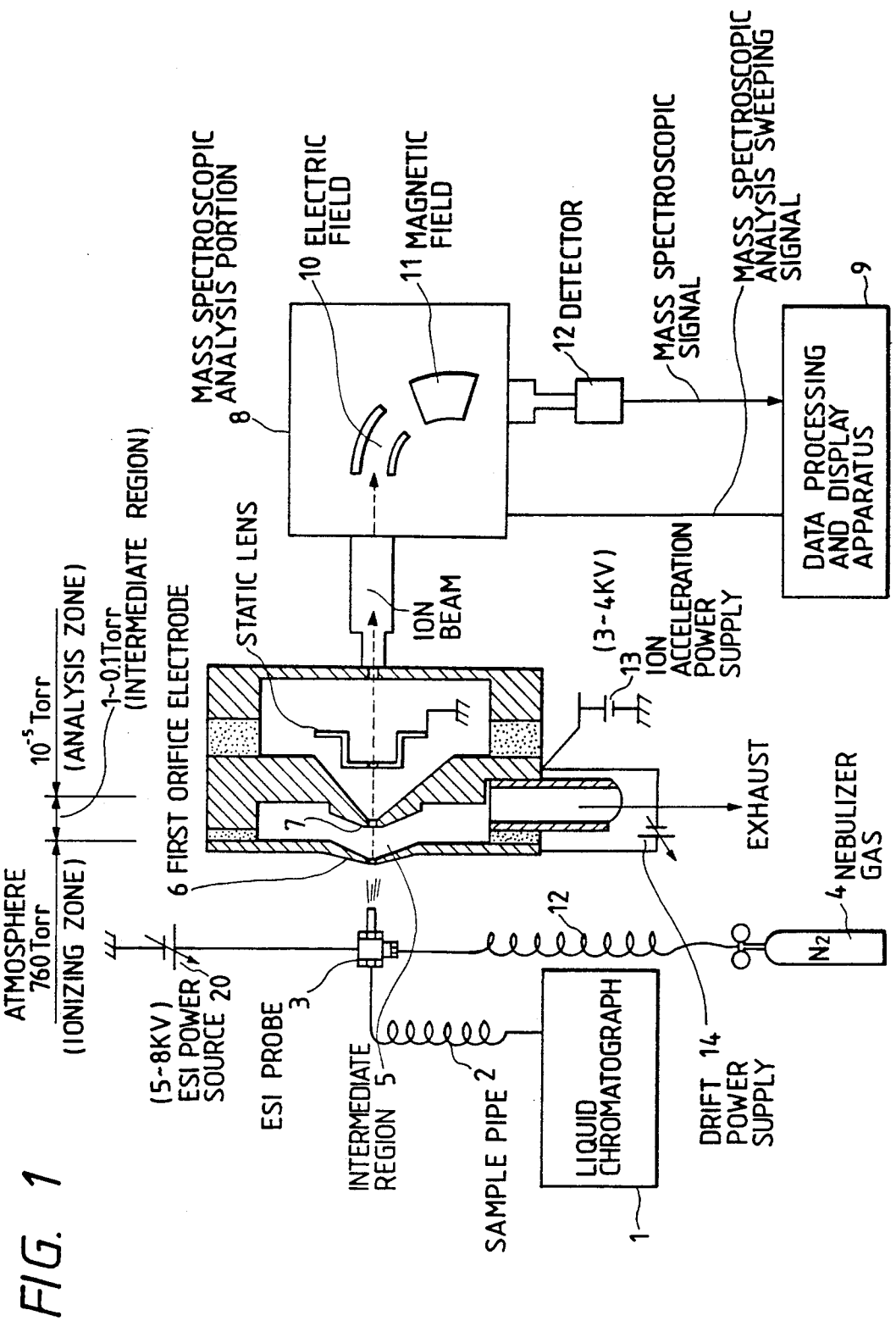
FIG. 1 is a schematic illustration of a partial section of a mass spectrometer relating to one of the embodiments of the present invention.

Referring to FIG. 1, a sample and a mobile phase which are eluates from the liquid chromatograph are transferred to the ESI probe 3 through the capillary tube 2, and subsequently, the eluates are nebulized at a top end of the ESI probe 3 with the assistance of a nebulizer gas ($N_2$) supplied from the nebulizer gas cylinder 4.

The above nebulized sample is ionized under a high electric field, accelerated and is passed through a small hole in the first electrode 6, and introduced into the medium pressure region 5 which is formed between the first electrode 6 and the second electrode 7. The electrostatic field is generated by the ESI power source 20, the ion acceleration power source 13, the drift power supply, and the static lens 25 etc.

The beginning of the nebulization, the eluate forms a small droplet in which the sample molecule is wrapped with the mobile phase (a film of eluent for the sample), and is ionized with a high electrostatic field (about 5-8 kV) which is charged to the capillary tube 2 by the ESI power supply 20.

A droplet of the nebulized sample gradually becomes small due to evaporation of the mobile phase component during transfer thereof to the first electrode 6 in an atmosphere under a pressure of substantially 760 Torr. and finally changes to a sample molecular ion.

That means, when the sample particle becomes small, a Coulomb repulsion between the sample ion and the mobile phase charge becomes larger than the surface tension of a fine droplet, and accordingly, the sample ion in the sample particle is released from the mobile phase layer of the droplet and changes to an ion composed of only the sample molecule. This phenomenon is called "ion evaporation" as previously described.

The sample molecular ion passes through the small hole in the first electrode 6, and then passes through the small hole in the second electrode 7, the static lens 25, and is transferred to the mass spectrometer portion 8 and analyzed by a mass spectrometer. That means, the sample molecular ions which are introduced into the mass spectrometer portion 8 are dispersed according to their velocities by the electric field 10 and in accordance with their masses by the magnetic field 11, and subsequently, ions having various mass numbers are orderly detected by the detector 12 by scanning the magnetic field 11. The detected ions are converted to electric signals, the signals are transmitted to the data processing and display apparatus 9 where they are processed to obtain a mass spectrum, and displayed. The mass spectrometer portion 8 side from the second electrode 7 is maintained at a reduced pressure of about $10^{-5}$ Torr.

During the mass spectrometry, the less the dispersed distribution of masses of the sample molecular ions is, the more will the analytical sensitivity be improved. Furthermore, the larger the ionization tendency of the sample is the higher will be the efficiency of the ion evaporation. Consequently, the above mass spectrometry is suitable for analyzing such high polymer samples having strong polarities of NH, OH, and CO etc as a peptide with a high sensitivity. Accordingly, such mass spectrometry has attracted much attention, especially in the field of medical analysis, as previously described.

Actually, sample molecules which are ionized by ion evaporation addictively have still a large number of mobile phase molecules, especially water molecules, and the sample molecular ions (cluster ions) having adsorbed water molecules pass through the small hole in the second electrode 7 although the water molecules are partially dissociated by collisions with neutral molecules when passing through the medium pressure region 5.

The sample molecular ions having adsorbed water molecules collide with neutral particles in a free space at an entrance of the electric field 10 in the mass spectrometry portion 8 and a following electric field, and the water molecules are dissociated.

The number of the dissociated water molecules from a sample molecule has been calculated from the width of kinetic energy of the sample molecular ions which pass through the electrostatic field 10 to be 30 to 60 molecules.

Similarly, the sample molecular ions dissociate water molecules by collisions with the neutral particles in the space from an outlet of the electrostatic field 10 to an outlet of the magnetic field 11.

Although a large number of water molecules are dissociated in a manner described above during a period until reaching the entrance of the magnetic field 11, if the residual amount of the water molecules is large, a dispersion of distribution in mass of the sample molecular ions becomes large, and consequently, the analytical sensitivity decreases because not all of the sample molecular ions are able to reach the detector 12.

Figure 2:
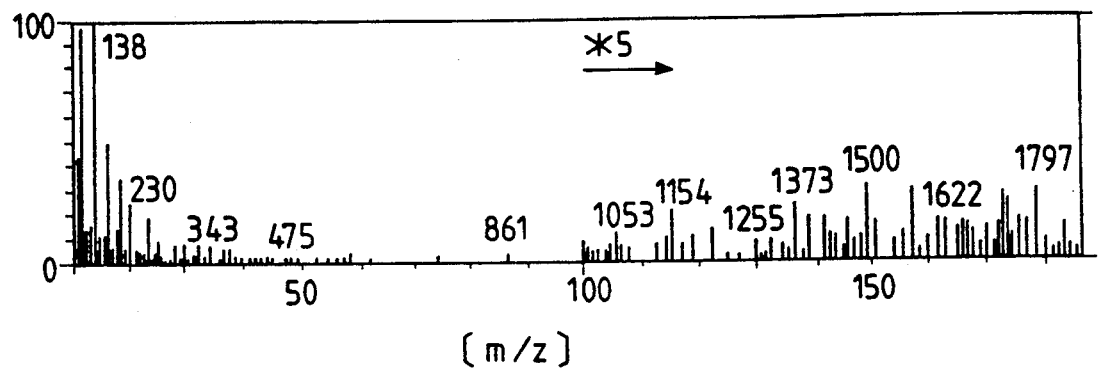
FIG. 2 is an example of a mass spectrum obtained by an example of conventional methods.

FIG. 2 is an example of mass spectrometry results on bovine-insulin by the same apparatus shown in FIG. 1, but without the heater 23 and in which the thickness of the small hole in the first electrode 6 is 0.2 mm. The above exception means that the result shown in FIG. 2 is an example of the results obtained by a conventional apparatus. Signals which should exist in a region, m/z=1000-1850, can not be discriminated owing to masking by a group of random ion peaks, and the above group of random ion peaks fluctuates with every measurement. Accordingly, it is apparent that no effective data can be obtained. A reason for the above deficiency is an insufficient dissociation of the above mobile phase and water molecules.

On the other hand, the apparatus shown in FIG. 1 has the heater 23 added to the first electrode 6 and the first electrode 6 has a small hole, the length of which is extended to about 5 mm, instead of the 0.2 mm of the previously described conventional apparatus.

The nebulized sample and the mobile phase, both of which are injected from a top end of the ESI probe 3, repeats evaporation of the mobile phase on droplets and breakage of the droplets to be smaller than before, and are ionized and reach the first electrode 6. Because the inside of the small hole in the first electrode 6 is heated by the heater 23, which is powered by the heater power supply 26, the sample molecular ions are also heated when they pass through the small hole, and accordingly, combinations of the sample molecular ions and water molecules are heated, and the sample molecular ions combined with water molecules are accelerated by the electric field in the medium pressure region 5. In particular, water molecules are dissociated from the sample molecular ions by collisions with the neutral molecules.

Practically, by setting a voltage between the first electrode 6 and the second electrode 7 which is charged by the drift power supply 14 at 100-150 V, the temperature of the first electrode 6 at 120° C., and a reduced pressure of the medium pressure region 5 at about 0.5 Torr, the mean free path of molecules becomes 0.1 mm, and consequently, the sample molecular ion collides with the neutral particles about 70 times during movement through a medium pressure region 5 of 7 mm in length.

In a manner as above described, the mobile phase molecules including water molecules are dissociated from the sample molecular ions by such a large number of collisions, that the sample molecular ions become isobar.

The higher the temperature of the first electrode is, the more the above dissociation occurs, but the more the values of the sample molecular ion peaks will decrease because of increasing thermal decomposition of the a sample molecular ions. Accordingly, a preferable range of the temperature setting of the first electrode 6 is 50° C.-140° C.

Reduced pressure in the medium pressure region 5 is kept between 0.1-1 Torr. The sample molecular ion which passes through the small hole in the first electrode at 50° C.-140° C. and reaches the medium pressure region 5 is given a necessary kinetic energy for the dissociation of water molecules effectively by the collision with the neutron particles in the medium pressure region 5. The mean free path of the sample molecular ion at this time is 0.05-0.5 mm.

When the vacuum at the intermediate pressure region becomes higher than 0.1 Torr (e.g. higher vacuum) and the voltage of the drift power supply 14 increases, a problem results in that peak intensities of multi-charged ions which are objects of the ESI ion analysis decrease comparatively; although peak intensities of less-charged ions increase. Further, when vacuum at the intermediate pressure region becomes lower than 1 Torr (e.g. lower vacuum), scattering of the sample ions in the intermediate pressure region 5 increases and the analytical sensitivity decreases rapidly. As above explained, there is an optimum range for the temperature of the first electrode 6 and the reduced pressure of the medium pressure region 5, respectively.

Figure 3:
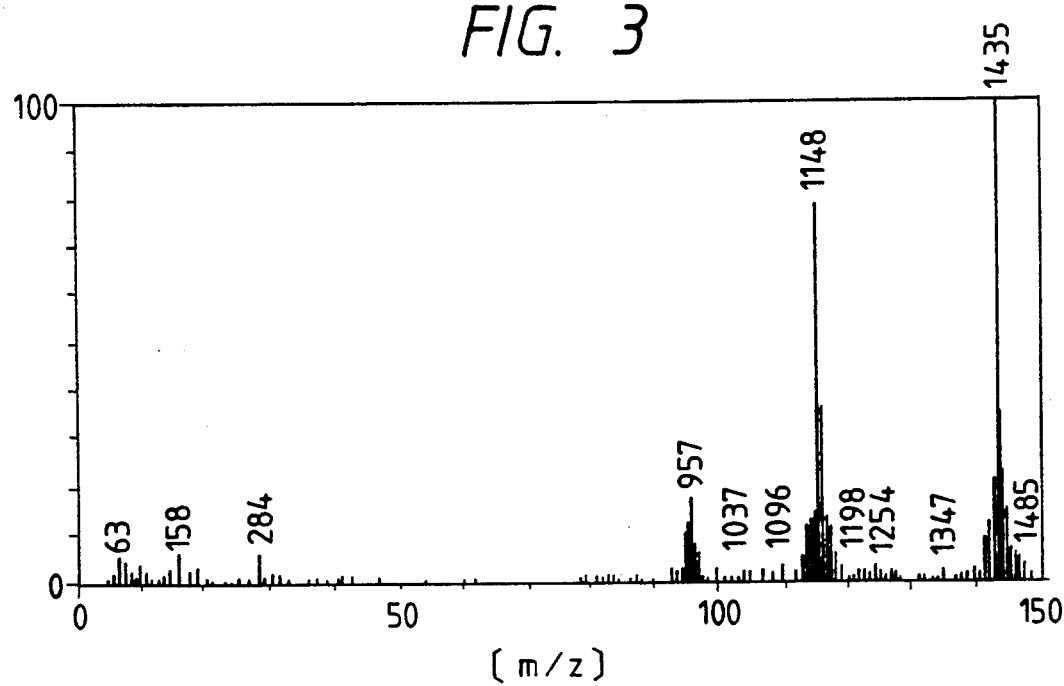
FIG. 3 is an example of a mass spectrum obtained by an embodiment of the present invention.

FIG. 3 is a mass spectrum of bovine-insulin in a case wherein the above optimum conditions are fulfilled. In comparison with FIG. 2 which shows conventional data, the typical mass spectra of the bovine-insulin are clearly observed at m/z=957, 1148, and 1435 etc.

$$r < (Tn - Td)^{\frac{1}{2}} \cdot X$$

where, r = Radius of an injected nebulized sample particle ($\mu$m)

Tn = Temperature of the first electrode (°C.)

Td = Temperature of the nebulized sample particle (°C.)

X = Length of the small hole in the first electrode (m)

The above equation is a theoretical equation which gives a range of the radius r of the injected nebulized sample particle wherein the mobile phase component is completely evaporated by passing through the first electrode 6. In accordance with the above equation, taking (Tn-Td) as 100° C. for example and X as 0.005 m in FIG. 1, the value of r becomes less than 0.05 $\mu$m and it is revealed that the mobile phase component in the nebulized sample particle having a radius in a range less than 0.005 $\mu$m can be completely evaporated.

On the contrary, in the previously described conventional example, X is as short as 0.0002 $\mu$m and (Tn-Td) is small because the heater is not furnished, and accordingly, it is assumed that this is the cause of the difference between FIG. 2 and FIG. 3.

Figure 4:
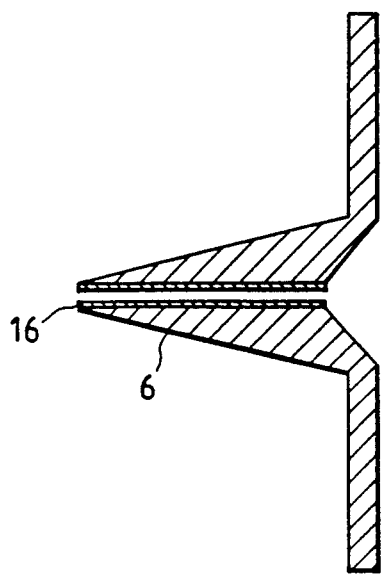
FIG. 4 is a cross section of another embodiment of a small hole portion in the first electrode shown in FIG. 1.

Now, consideration should be given to an optimum range of the values for length X of the small hole in the first electrode 6. It is obvious that preferable result can be expected by reducing the diameter and extending the length of the small hole, but practically there is a limit to drilling a small hole as a thickened portion of the first electrode. Accordingly, the capillary tube 16 having a desired inside diameter is utilized as shown in FIG. 4.

A vacuum leakage in the intermediate pressure region 5 is caused through the small hole in the first electrode 6. The amount of the leakage is proportional to the fourth power of the inside diameter of the small hole.

Accordingly, if the diameter is reduced from 0.5 mm to 0.1 mm, the amount of the leakage is reduced to about one six hundredth. Therefore, in view of the leakage, if the inside diameter of the small hole in the first electrode 6 is decreased, the length of the small hole can be reduced remarkably.

In the apparatus shown in FIG. 1, the minimum inside diameter of the small hole which can be easily drilled at the first electrode 6 is about 0.5 mm. However, in a case using the above capillary tube 16, the inside diameter of the small hole can be reduced to about 0.1 mm. Furthermore, the capillary tube is easily available, and if choosing a diameter less than 0.4 mm, the problem of vacuum leakage at the intermediate pressure region can be practically avoided.

The outer diameter of the pipe 16 is usually more than one sixteenth inches (1.58 mm), and an easy drilling length of a hole for inserting the pipe corresponding to the outer diameter at the first electrode 6 is about 50 mm. The capillary tube is inserted into the drilled hole and fixed with welding or silver soldering.

Figure 5:
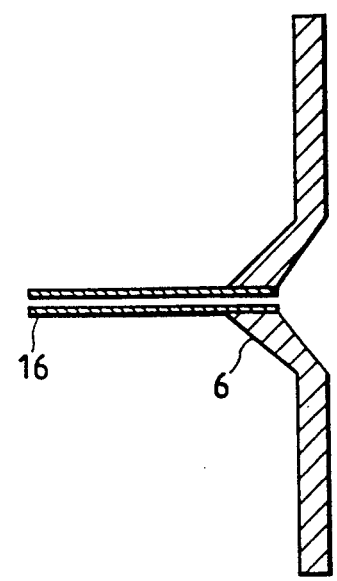
FIG. 5 is a cross section of a further embodiment of the small hole portion in the first electrode.

FIG. 5 illustrates a case in which an end of the pipe 16 is fixed to a hole in the relatively thin first electrode 6. In the above case, the length of the capillary tube which can be easily fixed to the electrode is also about 50 mm.

If the length of the pipe 16 is determined to be about 50 mm or less as above explained, a blockage of the capillary tube 16 by the sample is easily eliminated by a fine tungsten wire, maintenance of the first electrode portion is facilitated because the capillary tube 16 is not bent or damaged during cleaning, and the stopping time of the apparatus operation for maintenance becomes short. Accordingly, the throughput of the whole apparatus can be improved.

Furthermore, the inside of the pipe 16 can be cleaned by an ultrasonic wave. In the above case, it is necessary to detach the first electrode 6 and the heater 23 etc., but as the length of the pipe is short as 50 mm, it is as unlikely that the pipe will be broken during its handling.

As above explained, the problem such as extreme difficulties in cleaning and exchange of a small pipe in the apparatus disclosed in U.S. Pat. No. 4,977,320 can be completely resolved by shortening the length of the pipe 16.

Referring to FIG. 3, it has previously been explained that sufficient analytical sensitivity for high polymer analysis can be obtained even in the case when the length of the small hole of the first electrode 16 is short as 5 mm.

On the other hand one may consider the case when the length of the pipe 16 is extended to about 50 mm.

Figure 6:
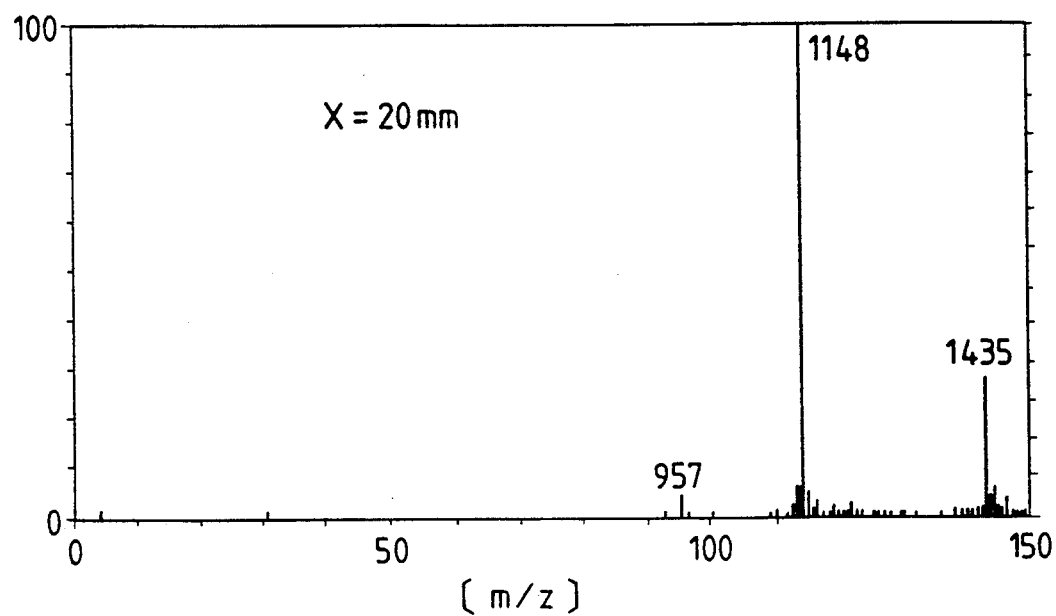
FIG. 6 is a mass spectrum obtained using the small hole portion (20 mm long) indicated in FIG. 5.
Figure 7:
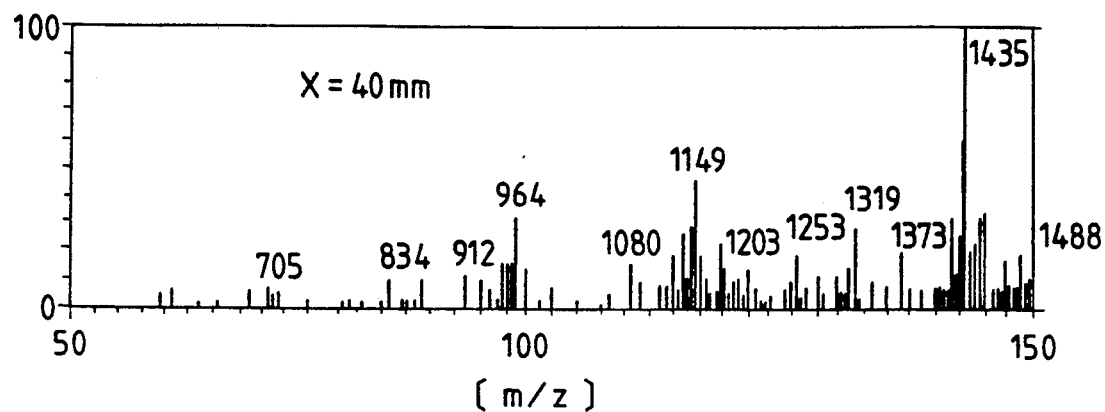
FIG. 7 is a mass spectrum obtained using the small hole portion (40 mm long) indicated in FIG. 5.

FIG. 6 is an analytical result on bovine-insulin in a case when the length of the pipe 16 is 20 mm, and FIG. 7 is a case of 40 mm. FIG. 6 indicates that a high sensitivity which can not be expected by conventional apparatus can be obtained by the present invention. However, FIG. 7 indicates remarkable decrease of the sensitivity, and reveals that an exceeding extension of the length of the pipe 16 decreases the sensitivity. Accordingly, it can be concluded that the limit of the pipe length is 50 mm.

The sensitivity can also be improved further by the method of heating the capillary tube 16.

That is, temperatures of the sample molecules decrease rapidly by adiabatic expansion in the capillary tube 16. On the other hand, if the capillary tube 16 is heated by conduction of heat from the first electrode 6, the temperature at the top end of the capillary tube becomes lowest and heating of the sample molecule becomes smallest, and consequently, an eliminating effect of the adsorbing molecules from the sample molecule is low.

Accordingly, the above deficiency can be overcome by relatively strong heating of the top end of the capillary tube 16.

Figure 8:
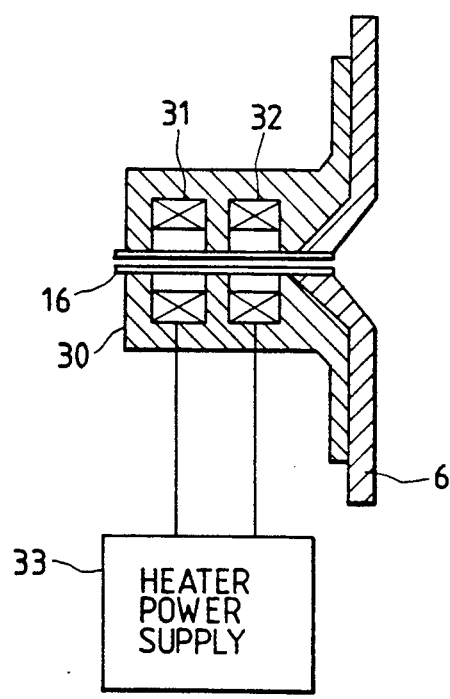
FIG. 8 is a cross section of a further embodiment of the small hole portion in the first electrode.

FIG. 8 is another embodiment of the present invention wherein a predetermined temperature distribution can be given to the whole length of the capillary tube 16.

Heaters are fixed to the pipe. The heater is composed of a metallic yoke 30 and a plurality of heating coils 31, 32 for example. An arbitrary temperature distribution can be given in a longitudinal direction of the pipe 16 by separately controlling power supplies to the heaters with the heater power supply 33.

The adiabatic expansion of the sample molecules does not necessarily occur homogeneously in the pipe 16. For instance, in the vicinity of the outlet of the pipe 16, the adiabatic expansion is assumed to be large because the vacuum degree at the portion is high. Furthermore, the adiabatic expansion is effected by the vacuum degree in the vicinity of the outlet, by the viscosity and by the average temperature of the sample gas.

Accordingly, in order to obtain the most preferable result, the temperature distribution of the capillary tube 16 must be determined experimentarily, and if necessary, the number of the above heating coils must be increased and each coil regulated separately.

The above heater is not necessarily restricted to the structure shown in FIG. 3, if the structure can realize an arbitrary temperature distribution in the pipe 16.

It is apparent that there are various modifications and changes without departing from the essentials of the present invention, and accordingly, the present invention should not be understood to be restricted by the above described details.

What is claimed is:

1. A mass spectrometer comprising:
   means for ionizing a sample so as to generate ions of the sample;
   a first electrode having a first hole through which said generated ions pass;
   a second electrode having a second hole through which said ions which have passed through said first hole pass;
   means for subjecting said ions which have passed through said second hole to mass spectrometry; and
   means for heating an inside of said first hole; wherein said first hole has a length of substantially at most 50 mm.

2. A mass spectrometer as claimed in claim 1, wherein said first electrode has a pipe which composes said first hole.

3. A mass spectrometer as claimed in claim 1, wherein said first hole has an inside diameter of substantially at most 0.4 mm.

4. A mass spectrometer as claimed in claim 1, wherein said first electrode has a pipe which composes said first hole; and
   said first hole has an inside diameter of substantially at most 0.4 mm.

5. A mass spectrometer as claimed in claim 1, wherein a setting range of temperature inside of said first hole is substantially between 50° C. and 140° C.

6. A mass spectrometer as claimed in claim 1, wherein said first electrode has a pipe which composes said first hole; and a setting range of temperature inside of said first hole is substantially between 50° C. and 140° C.

7. A mass spectrometer as claimed in claim 1, wherein
said first electrode has a pipe which composes said first hole; and
said first hole has an inside diameter of substantially at most 0.4 mm; and
a setting range of temperature inside of said first hole is substantially between 50° C. and 140° C.

8. A mass spectrometer as claimed in claim 1 or claim 2, wherein
said means for heating includes means for generating a predetermined temperature distribution in a longitudinal direction of the inside of said first hole.

9. A mass spectrometer as claimed in claim 8, wherein
said means for ionizing is an electro-spray ionization source.

10. A mass spectrometer as claimed in claim 9, further comprising:
means for charging a voltage between said first electrode and said second electrode so as to accelerate said ions which pass through an interval between said two electrodes; and
means for evacuating said interval between said two electrodes to vacuum in a range of substantially from 0.1 Torr. to 1 Torr.

11. A mass spectrometer as claimed in any one of claims 1 to 7, wherein
said means for ionizing includes an electro-spray ionization source.

12. A mass spectrometer as claimed in claim 9, further comprising:
means for charging a voltage between said first electrode and said second electrode so as to accelerate said ions which pass through an interval between said two electrodes; and
means for evacuating said interval between said two electrodes to vacuum in a range of substantially from 0.1 Torr. to 1 Torr.

13. A mass spectrometer comprising:
means for ionizing a sample so as to generate ions of the sample; a plurality of electrodes spaced along an ion path extending from said ionizing means, each of said electrodes having a hole through which said ions pass, said plurality of said electrodes having an electrode which is nearest to said ionizing means;
means for subjecting said ions which pass through said holes to mass spectrometry; and
means for heating an inside of the hole of the nearest electrode;
wherein said hole of the nearest electrode has a length of substantially at most 50 mm and an inside diameter of substantially at most 0.4 mm.

14. A mass spectrometer as claimed in claim 13, wherein
a setting range of temperature inside of said hole of the nearest electrode is substantially between 50° C. and 140° C.

15. A mass spectrometer as claimed in claim 14, wherein
said means for heating includes means for generating a predetermined temperature distribution in a longitudinal direction of the inside of said hole of the nearest electrode.

* * * * *